United States Patent
Kemp et al.

(10) Patent No.: US 8,853,454 B2
(45) Date of Patent: Oct. 7, 2014

(54) QUATERNARY AMMONIUM SALTS AS MICROBE INHIBITORS

(75) Inventors: Maurice C. Kemp, Cedar Park, TX (US); David E. Lewis, Eau Claire, WI (US)

(73) Assignee: Mionix Corporation, Austin, TX (US)

( * ) Notice: Subject to any disclaimer, the term of this patent is extended or adjusted under 35 U.S.C. 154(b) by 1435 days.

(21) Appl. No.: 12/377,883

(22) PCT Filed: Aug. 29, 2007

(86) PCT No.: PCT/US2007/018998
§ 371 (c)(1),
(2), (4) Date: Aug. 12, 2010

(87) PCT Pub. No.: WO2008/027430
PCT Pub. Date: Mar. 6, 2008

(65) Prior Publication Data
US 2010/0297207 A1    Nov. 25, 2010
US 2012/0034290 A9    Feb. 9, 2012

Related U.S. Application Data

(60) Provisional application No. 60/840,785, filed on Aug. 29, 2006, provisional application No. 60/926,399, filed on Apr. 26, 2007.

(51) Int. Cl.
| | | |
|---|---|---|
| C07C 209/20 | (2006.01) | |
| D21H 21/36 | (2006.01) | |
| A01N 33/12 | (2006.01) | |
| A01N 43/40 | (2006.01) | |
| C07C 211/63 | (2006.01) | |
| D21H 17/17 | (2006.01) | |
| D21H 17/07 | (2006.01) | |

(52) U.S. Cl.
CPC ............. *A01N 33/12* (2013.01); *C07C 209/20* (2013.01); *D21H 17/17* (2013.01); *D21H 21/36* (2013.01); *C07C 211/63* (2013.01); *A01N 43/40* (2013.01); *D21H 17/07* (2013.01)
USPC ........................................................ 564/296

(58) Field of Classification Search
USPC ........................................................ 564/296
See application file for complete search history.

(56) References Cited

U.S. PATENT DOCUMENTS

| | | | | |
|---|---|---|---|---|
| 5,399,762 A | * | 3/1995 | Walker .......................... | 564/296 |
| 5,599,990 A | * | 2/1997 | Miller et al. .................. | 564/296 |
| 5,696,292 A | * | 12/1997 | Cody et al. .................... | 564/296 |
| 6,414,159 B2 | * | 7/2002 | Sano et al. .................... | 546/347 |
| 6,664,224 B2 | * | 12/2003 | Kourai et al. ................. | 510/384 |
| 7,183,434 B2 | * | 2/2007 | Baan et al. .................... | 564/296 |

* cited by examiner

*Primary Examiner* — Brian J Davis
(74) *Attorney, Agent, or Firm* — Jackson Walker L.L.P.

(57) ABSTRACT

The present invention relates to quaternary ammonium salts and their use as mold inhibitors. The quaternary salts can be prepared by a chloride ion-promoted reaction between a tertiary amine and an alcohol or polyol in strong acid solution. The quaternary ammonium salts can be applied to a substrate in order to impart anti-mold properties to the substrate. Preferably, the quaternary ammonium salt compounds are applied to paper substrates in an amount of about 1000 ppm. Preferably, the quaternary ammonium salts compounds are applied as mixtures of more than one quaternary ammonium salt compound. The treated substrate does not require encapsulators, binders, or retention aids.

5 Claims, 1 Drawing Sheet

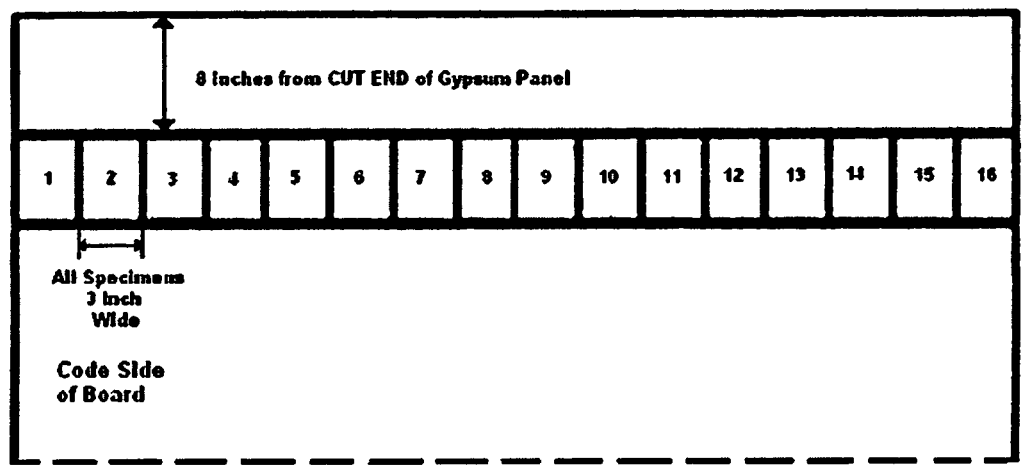

QUATERNARY AMMONIUM SALTS AS MICROBE INHIBITORS

This application claims priority to U.S. Provisional Patent Application Ser. No. 60/840,785, entitled "Quaternary Ammonium Salts as Microbe Inhibitors," filed on Aug. 29, 2006, and U.S. Provisional Patent Application Ser. No. 60/926,399, entitled "Quaternary Ammonium Salts as Microbe Inhibitors," filed on Apr. 26, 2007, the entire content of both being hereby incorporated by reference.

BACKGROUND

This invention pertains to microbe inhibitors and particularly to the use of quaternary ammonium salts applied on a substrate as inhibitors of microbial growth, and to the preparation thereof.

Water based polymer emulsions (such as latex emulsions) are susceptible to microbial contamination resulting in product spoilage. Polymer emulsions are dispersions of fine organic polymer particles in water. These polymer particles are suspended and stabilized in an aqueous environment with additional organic substrates, such as surfactants and protective colloids. Surfactants, protective colloids, such as poly (vinyl alcohol) and hydroxyethyl cellulose, thickeners and other additives, and the polymer itself all provide a supply of carbon nutrition for microorganisms to metabolize. Polymer emulsions are therefore susceptible to spoilage due to microbial attack and propagation.

One problematic microbe is mold. Mold is a term used to describe a type of fungus that typically grows on the surface of organic matter. More specifically, mold or fungus is a eukaryotic organism that digests its food externally and absorbs the nutrient molecules into its cells. Growth of mold on the surface of wallboard paper or in or on gypsum containing a carbohydrate source transpires when a spore comes into contact with the nutritional matrix. Mold growth ensues if the environmental and biological conditions are right. Initially, there is spore germination, then formation of hyphal growth, followed by spore formation and spore dispersion. In general, mold will not grow on the core component of wallboard. However, if a starch is added then nutrients are present and mold will grow if the gypsum matrix becomes wet and is exposed to mold spores.

Standard industrial practices combat such product biodeterioration by the addition of various industrial biocides (i.e. antimicrobial agents) directly after the manufacturing process. Examples of commonly used industrial biocides are: 1,2-benzisothiazolin-3-one ("BIT"), and a blend of 5-chloro-2-methyl-4-isothiazolin-3-one ("CIT") and 2-methyl-4-isothiazolin-3-one ("MIT"). Examples of other biocides commonly used for polymer emulsion preservation include 1,2-dibromo-2,4-dicyanobutane ("DBDCB"), 2,2-dibromo-3-nitrilopropionamide ("DBNPA"), 2-bromo-2-nitro-1,3-propanediol ("BNPD"), aldehyde derivatives, formaldehyde releasing agents, hydantoins, chlorinated aromatics, 2-(Thiocyanomethylthio)benzothiazole (CAS 6441-45-8, sold as Busan® and other names), Microban® (U.S. Pat. No. 6,767,647), and salt of pyrithione (U.S. Pat. No. 6,893,752).

These commonly used biocides are usually adequate to preserve various types of polymer emulsions against most industrial spoilage from bacteria and fungi. However, polymer emulsions stabilized with protective colloids, such as poly(vinyl alcohol) or hydroxyethyl cellulose, and/or nonionic surfactants, pose additional strains and challenges to many preservative systems. In general, it has been found that this class of polymer emulsion products is more susceptible to spoilage than other polymer emulsions by certain types of microbes. For example, biodeteriogenic microbes that can survive in acidic environments and/or that metabolize alcohols, such as *Gluconoacetobacter liquefaciens* ("GABL"), have begun to emerge and thrive in polymer emulsions, even in the presence of commonly used industrial biocides. Biodeteriogenic microbes include bacteria and fungi that can adversely affect the commercial value of products and materials. Some biodeteriogenic microbes have become so well adapted to the environment present in these emulsions, such as poly(vinyl alcohol)-stabilized poly(vinyl acetate-co-ethylene) copolymer emulsions, that the standard industrial biocides are inadequate to prevent product spoilage by this species over the entire product shelf life period; e.g., 6 to 12 months. A significant rise in polymer emulsion biodeterioration problems has resulted in a need to identify more effective preservative systems.

It is known that volatile organic compounds (VOC's"), such as unreacted monomers, in polymer emulsions exert some level of a bacteriostatic, if not bacteriocidal, effect, which can inhibit the growth of biodeteriogenic microbes. Recent developments in polymer emulsion technology, in response to regulatory issues and environmental concerns, have led to reductions in residual VOC and residual monomer levels. Such VOC reductions impact polymer emulsions in many ways. For example: (1) they create an emulsion environment more conducive to microbial growth, (2) they may permit the emergence of new microorganisms that find the new emulsion environment more hospitable, (3) they pose additional challenges to current preservative technologies, and (4) they create the need for new preservation methods to prevent biodeterioration over the products shelf life.

Although there are a significant number of biocides that can kill microorganisms effectively and can provide very good preservation for polymer emulsions and other industrial products, only a limited number of these exhibit acceptably low toxicity to higher organisms, e.g., humans. The choice of effective biocides that can be added to polymer emulsions becomes even more limited when United States Food and Drug Administration ("FDA") clearances are required for the polymer emulsion end use. Many polymer emulsions are used to manufacture consumer goods, such as adhesives and papers for food packaging, diapers, paper towels, baby wipes, and feminine hygiene products. As a result of such contact with skin and indirect contact with foods, the polymer emulsions used in these applications must have the appropriate FDA clearances. These FDA clearances are based on favorable toxicological profiles, including no skin sensitization. In order for a polymer emulsion to receive the necessary FDA clearances, all of its constituents, including the preservative technology, must meet the FDA's rigorous toxicological criteria when used at concentrations required for satisfactory performance in the polymer emulsion. FDA-approved biocides have use level restrictions. In some cases, the minimum biologically effective concentration is greater than the maximum allowable use level. Typically, this results in premature product biocontamination and biodeterioration. Additionally, microorganisms continue to evolve and new microorganisms are beginning to appear that exhibit resistance to some of the more common industrial biocidal agents, particularly at the allowable use level. A tightening regulatory environment, specific consumer good manufacturing specifications, public concern, and product liability, further complicate biocide selection and use. For example, isothiazolinones are widely used antimicrobial agents for many consumer products, but their known skin sensitization property causes concern among many consumer goods manufacturers. Such health concerns and microbial resistance are leading to a search for preservation alternatives and new preservation approaches.

Cationic compounds, such as quaternary ammonium compounds, are well known in the antimicrobial art and are widely used as disinfectants for surfaces. For example, they are used to disinfect floors, walls, countertops, equipment surfaces, food contact surfaces, and the like in hospitals, schools, nursing homes, restaurants, and residential homes. Furthermore, combinations of detergents with cationic compounds are widely used formulations for cleaning and disinfecting or sanitizing such surfaces with a single product. Cationic compounds are also used to inhibit the growth of algae and microorganisms in water, such as in swimming pools. Cationic compounds have been utilized on a limited basis for the preservation of industrial products and to prevent microbial growth in aqueous systems.

Cationic compounds, such as quaternary ammonium compounds, are usually prepared by the reaction between an amine and a suitable electrophile. Suitable electrophiles that have been used include alkyl halides and substituted epoxides.

Great Britain Patent No. 1,091,049 (1967) discloses the preparation of bacteriostatic tissue paper by incorporating alkylated guanidine salts during the tissue paper manufacturing process. The guanidine salt is introduced into the paper pulp slurry prior to sheet formation.

U.S. Pat. No. 3,970,755 (Gazzard et al., 1976) discloses biocidal compositions for aqueous systems comprising lauryl benzyl dimethyl ammonium chloride or cetyl trimethyl ammonium chloride, and 1,2-benzoisothiazolin-3-ones.

U.S. Pat. No. 4,661,503 (Martinet al., 1987) discloses a synergistic biocide composition of n-dodecylguanidine hydrochloride ("DGH") and a mixture of 5-chloro-2-methyl-4-isothiazolin-3-one and 2-methyl-4-isothiazolin-3-one for treating industrial process waters to prevent the growth of gram negative bacteria and fungi.

U.S. Pat. No. 4,725,623 (Whitekettle et al., 1988) discloses a bactericidal composition for aqueous systems comprising a synergistic aqueous mixture of 2-bromo-2-nitropropane-1,3-diol and n-dodecylguanidine.

U.S. Pat. No. 4,906,385 (Lyons, et al., 1990) discloses the use of water soluble C8-C18 alkyl guanidine salts, especially n-dodecylguanidine hydrochloride, for controlling macroinvertebrate biofouling of industrial cooling water system.

U.S. Pat. No. 5,041,463 (Whitekettle et al., 1991) discloses a bactericidal composition for aqueous systems, such as pulp and paper mill systems, comprising a combination of glutaraldehyde and dodecylguanidine hydrochloride.

U.S. Pat. No. 5,457,083 (Muia et al., 1995) discloses synergistic antimicrobial compositions containing polyether polyamino methylene phosphonates ("PAPEMP") and one or more non-oxidizing biocide, such as didecyl dimethyl ammonium chloride, dodecylguanidine hydrochloride, methylene bisthiocyanate, and 5-chloro-2-methyl-4-isothiazolin-3-one. The combination is reported to be useful in aqueous systems in a variety of industrial applications, such as papermaking, paints, adhesives, latex emulsions, and joint cements. Examples show that addition of PAPEMP to a non-oxidizing biocide improves bacterial kills in an aqueous system over 24 hour period.

U.S. Pat. No. 6,680,127 (Capps, 2004) describes a gypsum board having antifungal properties obtained through the addition of a controlled-release antifungal agent. The agent is cetylpyridinium chloride ("CPC"), which is a relatively small molecule having a relatively large alkyl side chain (C=16). The use of this relatively small molecule is ideal for this technology because the CPC is mixed with the gypsum powder in water to create the gypsum board, and molecules with longer alkyl side chains have reduced solubility in water. In addition, the patented gypsum board possesses a relatively large quantity of CPC, on the order of 0.01 to 1.5 weight percent of the dry weight of the gypsum in the board. The patented gypsum board also includes one or more encapsulators, binders, and retention aids. The retention aids used in the gypsum board include cationic, anionic and nonionic surfactants, polyacrylamides, polyamines, polyethyleneimines, cellulosic ethers, aldohexoses, starch, and combinations thereof.

U.S. Pat. No. 6,890,969 (Rabasco et al., 2005) describes compositions containing colloid-stabilized polymer emulsions and cationic compounds that are resistant to contamination with biodeteriogenic microbes. Examples of suitable microbicidal cationic compounds are: substituted pyridinium salts, substituted guanidine salts, tetrasubstituted ammonium salts, and polymeric cationic compounds.

U.S. Patent Publication No. 20040033343 pertains to mold-resistant corrugated cardboard that can be used in home construction. The cardboard includes liners which are infused with biocides such as 5-chloro-2-methyl-4-isothiazolin-3-one, hypochlorite and sodium hydroxide and sodium bromide. An additional medium between the liners can also include the biocides 1,2-benzothiazol-3(2H)-one and poly[oxyethylene(dimethyliminio)ethylene dichloride].

El-Zayat and Omran, "Disinfectants Effect on the Growth and Metabolism of *Acetobacter aceti*" (*Egypt J-Food-Sci.*, 11(1-2), 1983, pages 123-128) evaluates quaternary ammonium compounds, such as cetyl trimethylammonium bromide, as disinfectants against the growth and metabolism of *Acetobacter aceti*.

*Handbook of Biocide and Preservative Use*, Edited by H. W. Brancq and Boiteux, Rossmore, Blackie Academic & Professional, 1995, pages 361-362, describes biocidal surfactants for preservation of cosmetics and toiletries. Quaternary amines are reported to be potent antimicrobial substances.

U.S. Pat. No. 6,664,224 (Kourai, et al., 2003) discloses a method for the preparation of quaternary ammonium salts by the reaction between a tertiary amine and an U.S. Pat. No. 5,561,187 alkyl halide (chloride, bromide or iodide).

U.S. Pat. No. 6,414,159 (Sano, et al., 2002) discloses a method for the preparation of a quaternary ammonium halide by the reaction between a pyridine or N-alkylimidazole with an alkyl halide at high temperature.

U.S. Pat. No. 5,508,454 (Brancq and Boiteux, 1996) discloses a method for the preparation of a complex quaternary ammonium cation by alkylation of a tertiary amine with sodium chloroacetate.

U.S. Pat. No. 5,561,187 (Bechara and Baranowski, 1996) discloses a method for the preparation of a quaternary ammonium cation with two hydroxylated side chains by the acid-catalyzed reaction between a (hydroxyalkyl)dialkylamine and an epoxide.

U.S. Pat. No. 6,767,647 (Swofford et al., 2004) discloses a wallboard with antimicrobial characteristics. The wallboard may contain sodium pyrithione.

U.S. Pat. No. 6,893,752 (Veeramasuneni et al., 2005) discloses a gypsum panel that may contain a water-soluble pyrithione salt.

A need remains for a method of protecting polymer emulsions, especially those stabilized with hydroxyl-containing protective colloids and those with low VOC's, against product biodeterioration by microbes. There is also a need for polymer emulsion compositions which are resistant to biodeterioration over their shelf life (about 6 to 12 months).

Further, a need remains for a cost-effective method for the preparation of quaternary ammonium salts directly from alcohol precursors.

SUMMARY

The present invention pertains to quaternary ammonium salts, their preparation, and their uses as inhibitors of microbial growth in particular substrates.

Quaternary ammonium salts are salts that consist of a quaternary ammonium cation and an anion. Quaternary ammonium cations, also known as quats, are positively charged polyatomic ions of the structure $NR_4^+$ with R being alkyl groups. Any of the four alkyl groups may be the same or different alkyl groups, and, in the case of heterocyclic quaternary salts such as N-alkylpyridinium salts, two of the R groups may correspond to a π bond to the same atom. Also, any of the alkyl groups can be connected, resulting in a cyclic structure. Unlike the ammonium ion $NH_4^+$ itself and primary, secondary, or tertiary ammonium cations, the quaternary ammonium cations are permanently charged, regardless of the pH of their solution. Quaternary ammonium cations are synthesized by exhaustive alkylation of ammonia or other amines.

Quaternary ammonium compounds are surface-active compounds that tend to take up and hold on to surfaces of other substances. The quaternary ammonium groups of these salts provide the exchange sites on certain anion exchange resins. Quaternary ammonium salts in which the "active" ingredient is sufficiently high in activity and concentration can be used in water treatment as microbiocides and surfactants. Cationic quaternary ammonium compounds are adsorbed by the cell membranes of the microbes and form ion pairs with the negative charges carried by the cell walls to inactivate and kill the microorganism.

The current invention pertains to quaternary ammonium salt compounds with the structure:

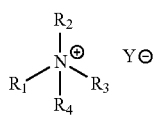

wherein:
R₁ is a straight-chain or branched-chain alkyl group, $C_nH_{2n+1}$, where 8≤n≤30;
R₂ is an alkyl group selected from the group consisting of
 (a) straight-chain or branched-chain alkyl groups, $C_nH_{2n+1}$, where 1≤n≤6; (b) cycloalkyl groups or alkyl substituted cycloalkyl groups, $C_nH_{2n-1}$, where 3≤n≤10, and (c) benzyl or substituted benzyl groups;
R₃ is an alkyl group selected from the group consisting of
 (a) straight-chain or branched-chain alkyl groups, $C_nH_{2n+1}$, where 1≤n≤6, (b) cycloalkyl or alkyl substituted cycloalkyl groups, $C_nH_{2n-1}$, where 3≤n≤10, and (c) benzyl or substituted benzyl groups;
R₄ is an ω-hydroxyalkyl group $[(CH_2)_mO]_nH$, where 2≤m≤6 and 1≤n≤4; and
Y is a halide anion, a hydrogen sulfate anion, hydroxide anion, bicarbonate anion, carbonate anion, a carboxylate anion containing up to 18 carbon atoms, lactate anion, tartrate anion, gluconate anion, saccharinate anion, an alkanesulfonate anion, an arenesulfonate anion, phosphate ion, hydrogen phosphate ion, or dihydrogen phosphate ion, or a mixture of two or more of these ions.

Preferably, R₁ is a straight-chain or branched-chain alkyl group, $C_nH_{2n+1}$, where 17≤n≤30.

Preferably Y is chloride or hydrogen sulfate, or a mixture of both these anions.

The current invention also pertains to quaternary ammonium salts containing the cation:

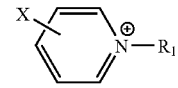

wherein:
R₁ is a straight-chain or branched-chain alkyl group, $C_nH_{2n+1}$, where 8≤n≤30; and
X is selected from the group consisting of (a) hydrogen, (b) straight-chain or branched-chain alkyl groups, $C_nH_{2n+1}$, where 1≤n≤6, (c) cycloalkyl or alkyl substituted cycloalkyl groups, $C_nH_{2n-1}$, where 3≤n≤10, (d) derivatized carboxyl groups such as esters or amides, (e) halogens such as Cl, Br, or I, and (f) dialkylamino groups, $NR_2$, where R is an alkyl group with 4 carbons or less.

Preferably, R₁ is a straight-chain or branched-chain alkyl group, $C_nH_{2n+1}$, where 17≤n≤30.

The current invention also pertains to the use of these quaternary ammonium salts, particularly as mixtures of more than one type of quaternary ammonium salt, as a treatment to impart microbial resistance to a substrate. Preferably, the quaternary ammonium salts are used as mixtures containing at least two different quaternary ammonium salts as major components in each application. The current invention also pertains to a substrate having anti-microbial properties that has been treated with the quaternary ammonium salts. The quaternary ammonium salts are effective even at very low concentrations.

The current invention also pertains to a method for the synthesis of these quaternary ammonium salts, comprising the following steps:
1. An alcohol, $R_4$—OH, preferably where $R_4$ is defined as follows, is cooled, preferably below 10° C., most preferably to approximately 2° C.-6° C.;
 where $R_4$ is: (a) an ω-hydroxyalkyl group having the formula $[(CH_2)_mO]_nH$, wherein 2≤m≤6 and 1≤n≤4; (b) a saturated alkyl or cycloalkyl group, containing 2-8 carbon atoms; (c) an unsaturated alkyl or cycloalkyl group, containing 3-8 carbons; or (d) an arylalkyl group, consisting of an aromatic ring and an alkylene group with 1-6 carbons;
2. The cooled alcohol is mixed with a strong acid, preferably sulfuric acid. The acid should also be cooled below 10° C., preferably to approximately 2-6° C. The molar ratio of hydrogen ions to alcohol in the mixture resulting from addition of the strong acid to the alcohol is approximately between 0.1 and 10, preferably between 0.5 and 2.
3. The alcohol-strong acid mixture is then added to a metal halide (such as sodium chloride) solution containing of halide ions, in sufficient water to facilitate mixing.
4. The resultant mixture is stirred until it is homogeneous or uniform;
5. A tertiary amine ($R_1$—$NR_2R_3$, where R₁, R₂, and R₃ are defined as follows), is added to the mixture with stirring, most preferably where the ratio of the molar equivalent of the tertiary amine to the alcohol is approximately between 0.1 and 10;
 where R₁ is a straight-chain or branched-chain alkyl group having the formula $C_nH_{2n+1}$, 17≤n≤30;

where $R_2$ is an alkyl group selected from the group consisting of (a) straight-chain or branched-chain alkyl groups having the formula $C_nH_{2n+1}$, wherein $1 \le n \le 6$; (b) cycloalkyl groups or alkyl substituted cycloalkyl groups having the formula $C_nH_{2n-1}$, wherein $3 \le n \le 10$, and (c) benzyl or substituted benzyl groups;

where $R_3$ is an alkyl group selected from the group consisting of (a) straight-chain or branched-chain alkyl groups having the formula $C_nH_{2n+1}$, wherein $1 \le n \le 6$, (b) cycloalkyl or alkyl substituted cycloalkyl groups having the formula $C_nH_{2n-1}$, wherein $3 \le n \le 10$, and (c) benzyl or substituted benzyl groups.

6. The resultant mixture is heated, preferably to approximately 60-120° C., most preferably to approximately 80-90° C., to complete the reaction.

7. If an anion other than halide or hydrogen sulfate is required, an aqueous solution of the quaternary ammonium salt is passed through a column containing sufficient anion ion exchange resin to allow complete exchange of the anion. The new quaternary ammonium salt containing the desired anion is then recovered by evaporation of the excess solvent, or by removal of sufficient solvent to give a solution of the desired concentration.

8. Alternatively, the chloride or hydrogen sulfate salt of the quaternary ammonium ion is dissolved in water, and the solution is treated with sufficient solution containing a metal ion capable of precipitating the chloride or sulfate anion. The precipitate is removed by filtration or centrifugation, and the filtrate or supernatant is concentrated to the desired concentration.

9. The exchange of hydrogen sulfate for a basic anion such as carbonate, bicarbonate, or hydroxide is accomplished by dissolving the quaternary ammonium salt in water, and adding sufficient quantity of an aqueous solution of a metal hydroxide or carbonate to cause complete neutralization of the hydrogen sulfate, plus 1.0 equivalents of the monobasic base or 0.5 equivalents of the dibasic base, preferably of a metal hydroxide that will form a precipitate with the halide or sulfate ions.

10. Alternatively, the carbonate and bicarbonate salts of the quaternary ammonium cation are obtained by dissolving the quaternary ammonium hydroxide solution in water and passing carbon dioxide gas into the solution until either 0.5 mole equivalents of gas are absorbed (to give the carbonate), or until 1.0 mole equivalents of carbon dioxide gas are absorbed (to give the bicarbonate salt).

11. Alternatively, the quaternary ammonium hydroxide is formed by dissolving the quaternary ammonium halide or hydrogen sulfate in water, and subjecting the solution to electrolysis until 0.5 mole equivalents of the free halogen or oxygen gas has been formed.

BRIEF DESCRIPTION OF THE DRAWINGS

FIG. 1 shows the position of specimens on a wallboard sheet during testing.

DETAILED DESCRIPTION OF PREFERRED EMBODIMENTS

The present invention relates to quaternary ammonium salts and their use as microbial inhibitors on or in a substrate. The substrate may comprise paper, gypsum board, drywall, plasterboard, gibralter board, gib, rock lath, gypsum panels, including SHEETROCK® Brand gypsum panels (USG Corpation, Chicago Ill.), gyprock, rigips, assembled wall board with paper applied thereon, a combination thereof, or any other solid material capable of having salt applied to it.

One aspect of the present invention is a quaternary ammonium salt compound with the structure:

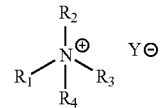

wherein:
$R_1$ is a straight-chain or branched-chain alkyl group having the formula $C_nH_{2n+1}$, wherein $8 \le n \le 30$;

$R_2$ is an alkyl group selected from the group consisting of (a) straight-chain or branched-chain alkyl groups having the formula $C_nH_{2n+1}$, wherein $1 \le n \le 6$; (b) cycloalkyl groups or alkyl substituted cycloalkyl groups having the formula $C_nH_{2n-1}$, wherein $3 \le n \le 10$, and (c) benzyl or substituted benzyl groups;

$R_3$ is an alkyl group selected from the group consisting of (a) straight-chain or branched-chain alkyl groups having the formula $C_nH_{2n+1}$, wherein $1 \le n \le 6$, (b) cycloalkyl or alkyl substituted cycloalkyl groups having the formula $C_nH_{2n-1}$, wherein $3 \le n \le 10$, and (c) benzyl or substituted benzyl groups;

$R_4$ is an $\omega$-hydroxyalkyl group having the formula $[(CH_2)_mO]_nH$, wherein $2 \le m \le 6$ and $1 \le n \le 4$; and Y is a halide anion, a hydrogen sulfate anion, hydroxide anion, bicarbonate anion, carbonate anion, a carboxylate anion containing up to 18 carbon atoms, lactate anion, tartrate anion, gluconate anion, saccharinate anion, an alkanesulfonate anion, an arenesulfonate anion, phosphate ion, hydrogen phosphate ion, or dihydrogen phosphate ion, or a mixture of two or more of these ions.

Preferably, $R_1$ is a straight-chain or branched-chain alkyl group, $C_nH_{2n+1}$, where $17 \le n \le 30$.

Preferably Y is chloride or hydrogen sulfate, or a mixture of both these anions.

If an anion other than halide or hydrogen sulfate is required, this may be incorporated by ion exchange of the halide or hydrogen sulfate salt with the appropriate anion. In this method, an aqueous solution of the quaternary ammonium salt is passed through a column containing sufficient anion ion exchange resin to allow complete exchange of the anion. The new quaternary ammonium salt containing the desired anion is then recovered by evaporation of the excess solvent, or by removal of sufficient solvent to give a solution of the desired concentration.

Alternatively, the exchange of the halide or hydrogen sulfate anion may be accomplished by a metathesis reaction in which a soluble metal salt of the desired anion is treated with the halide or hydrogen sulfate to generate a precipitate of the insoluble metal sulfate and a solution containing the desired anion. The precipitate may then be removed by filtration or centrifugation. For example, the hydrogen sulfate salt of the quaternary ammonium ion could be treated with one mole of calcium lactate per mole of quaternary ammonium hydrogen sulfate to give very sparingly soluble calcium sulfate and the lactate salt of the quaternary ammonium ion. Removal of the calcium sulfate precipitate by filtration or centrifugation is then followed by concentration of the filtrate or supernatant to the desired concentration.

Alternatively, the exchange of hydrogen sulfate for a basic anion such as carbonate, bicarbonate, or hydroxide may be accomplished by neutralization of the hydrogen sulfate anion with hydroxide ion or carbonate ion. For example, the hydrogen sulfate salt of a quaternary ammonium ion is treated with barium hydroxide solution (one mole of barium hydroxide per mole of quaternary ammonium hydrogen sulfate) to give the quaternary ammonium hydroxide and insoluble barium sulfate. The barium sulfate is removed by filtration or centrifugation, and the filtrate or supernatant is then concentrated by evaporation to the desired concentration.

Alternatively, the carbonate and bicarbonate salts of the quaternary ammonium cation may be obtained by allowing the solution of the quaternary ammonium hydroxide to absorb 0.5 moles of carbon dioxide per mole of quaternary ammonium ion (to give the carbonate) or 1.0 moles of carbon dioxide per mole of quaternary ammonium ion (to give the bicarbonate).

Alternatively, the formation of the quaternary ammonium hydroxide mat be accomplished by electrolysis of the solution of the quaternary ammonium halide solution to give the halogen and the quaternary ammonium hydroxide.

A further aspect of the present invention is a quaternary ammonium salt compound containing the cation:

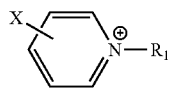

wherein:
R$_1$ is a straight-chain or branched-chain alkyl group having the formula $C_nH_{2n+1}$, wherein $8 \le n \le 30$; and
X is selected from the group consisting of (a) hydrogen, (b) straight-chain or branched-chain alkyl groups having the formula $C_nH_{2n+1}$, wherein $1 \le n \le 6$, (c) cycloalkyl or alkyl substituted cycloalkyl groups having the formula $C_nH_{2n-1}$, wherein $3 \le n \le 10$, (d) derivatized carboxyl groups, (e) halogens, and (f) dialkylamino groups having the formula $NR_2$, wherein R is an alkyl group with 4 carbons or less.

Preferably, R$_1$ is a straight-chain or branched-chain alkyl group, $C_nH_{2n+1}$, where $17 \le n \le 30$. X may be derivatized carboxyl groups such as esters or amides. X may also be halogens such as Cl, Br, or I.

Most of the quaternary ammonium salt compounds dissolve readily in water, although they have different viscosities in aqueous solution, and different solubilities. They also demonstrate microbe-inhibiting effects at different dilution levels. The quaternary ammonium salt compounds of this invention are capable of achieving microbe inhibition at surprisingly low concentrations. These concentrations can range from about 250 ppm to about 2000 ppm.

A further aspect of the current invention is the use of a mixture of more than one type of quaternary ammonium salt compound on a substrate in order to convey anti-microbial properties.

An additional aspect of the current invention is a method of imparting anti-microbial properties to a substrate by treating the substrate with the quaternary ammonium salt compounds. The term "treating" means dipping, spraying, coating, applying on, or any other method by which a substrate may come into contact with the quaternary ammonium salt compounds. Examples of substrates that are ideally suited to be treated with the quaternary ammonium salt compounds include all cellulose compositions and particularly paper. In addition, the quaternary ammonium salt compounds can be mixed with surface preparation materials such as paints. They can also be mixed with grouts or ceramic type materials and can be applied to protein materials such as silk and hair wool. They can be used to coat silicates that can be blown into extruded glass fibers to make, for example, insulation materials. The quaternary ammonium salt compounds can be blended with paper based insulation materials to prevent mold or microbial growth. The application rate of the quaternary ammonium salt compounds preferably does not exceed 1000 ppm of the final paper product. They can additionally be used to treat wood products such as plywood and structural woods to prevent molding or microbial growth. Quaternary ammonium salts can also be added to materials such as clay, gypsum, and even corn meal to prevent mold or microbial growth.

A further aspect of the current invention is a substrate having anti-mold properties that has been treated with the quaternary ammonium salt compounds.

The substrates treated with the quaternary ammonium salt compounds of the present invention do not require any additional ingredients or components to be effective. In particular, they do not include encapsulators, binders, or retention agents. While the preparation of the quaternary ammonium salt compounds may involve the use of surfactants to improve solubility and viscosity so that they may be effectively applied to the substrate, these ingredients do not need to be retained in the substrate for any purpose.

In addition, the quaternary ammonium salt compounds used to treat the substrates are not intended for controlled release. They are effective at inhibiting the growth of mold while being immediately available and do not require any delayed release features.

A further aspect of the current invention is a method for the preparation of quaternary ammonium salts by the halide ion promoted alkylation of a tertiary amine by an alcohol or polyol in strong acid solution by cooling an alcohol or polyol, mixing the cooled alcohol or polyol with a strong acid, adding a solution of a metal halide in water, and stirring until the mixture is homogeneous. A tertiary amine is added to this solution, and the mixture is stirred and heated until the reaction is complete.

In a preferred embodiment, a method for the synthesis of these quaternary ammonium salts, may comprise the following steps:
1. An alcohol, R$_4$—OH, preferably where R$_4$ is defined as follows, is cooled, preferably below 10° C., most preferably to approximately 2° C.-6° C.;
    where R$_4$ is: (a) an co-hydroxyalkyl group having the formula $[(CH_2)_mO]_nH$, wherein $2 \le m \le 6$ and $1 \le n \le 4$; (b) a saturated alkyl or cycloalkyl group, containing 2-8 carbon atoms; (c) an unsaturated alkyl or cycloalkyl group, containing 3-8 carbons; or (d) an arylalkyl group, consisting of an aromatic ring and an alkylene group with 1-6 carbons;
2. The cooled alcohol is mixed with a strong acid, preferably sulfuric acid. The acid should also be cooled below 10° C., preferably to approximately 2-6° C. The molar ratio of hydrogen ions to alcohol in the mixture resulting from addition of the strong acid to the alcohol is approximately between 0.1 and 10, preferably between 0.5 and 2.
3. The alcohol-strong acid mixture is then added to a metal halide (such as sodium chloride) solution containing of halide ions, in sufficient water to facilitate mixing.
4. The resultant mixture is stirred until it is homogeneous or uniform;
5. A tertiary amine (R$_1$—NR$_2$R$_3$, where R$_1$, R$_2$, and R$_3$ are defined as follows), is added to the mixture with stirring, most preferably where the ratio of the molar equivalent of the tertiary amine to the alcohol is approximately between 0.1 and 10;

where $R_1$ is a straight-chain or branched-chain alkyl group having the formula $C_nH_{2n+1}$, $17 \leq n \leq 30$;

where $R_2$ is an alkyl group selected from the group consisting of (a) straight-chain or branched-chain alkyl groups having the formula $C_nH_{2n+1}$, wherein $1 \leq n \leq 6$; (b) cycloalkyl groups or alkyl substituted cycloalkyl groups having the formula $C_nH_{2n-1}$, wherein $3 \leq n \leq 10$, and (c) benzyl or substituted benzyl groups;

where $R_3$ is an alkyl group selected from the group consisting of (a) straight-chain or branched-chain alkyl groups having the formula $C_nH_{2n+1}$, wherein $1 \leq n \leq 6$, (b) cycloalkyl or alkyl substituted cycloalkyl groups having the formula $C_nH_{2n-1}$, wherein $3 \leq n \leq 10$, and (c) benzyl or substituted benzyl groups.

6. The resultant mixture is heated, preferably to approximately 60-120° C., most preferably to approximately 80-90° C., to complete the reaction.

7. If an anion other than halide or hydrogen sulfate is required, an aqueous solution of the quaternary ammonium salt is passed through a column containing sufficient anion ion exchange resin to allow complete exchange of the anion. The new quaternary ammonium salt containing the desired anion is then recovered by evaporation of the excess solvent, or by removal of sufficient solvent to give a solution of the desired concentration.

8. Alternatively, the chloride or hydrogen sulfate salt of the quaternary ammonium ion is dissolved in water, and the solution is treated with sufficient solution containing a metal ion capable of precipitating the chloride or sulfate anion. The precipitate is removed by filtration or centrifugation, and the filtrate or supernatant is concentrated to the desired concentration.

9. The exchange of hydrogen sulfate for a basic anion such as carbonate, bicarbonate, or hydroxide is accomplished by dissolving the quaternary ammonium salt in water, and adding sufficient quantity of an aqueous solution of a metal hydroxide or carbonate to cause complete neutralization of the hydrogen sulfate, plus 1.0 equivalents of the monobasic base or 0.5 equivalents of the dibasic base, preferably of a metal hydroxide that will form a precipitate with the halide or sulfate ions.

10. Alternatively, the carbonate and bicarbonate salts of the quaternary ammonium cation are obtained by dissolving the quaternary ammonium hydroxide solution in water and passing carbon dioxide gas into the solution until either 0.5 mole equivalents of gas are absorbed (to give the carbonate), or until 1.0 mole equivalents of carbon dioxide gas are absorbed (to give the bicarbonate salt).

11. Alternatively, the quaternary ammonium hydroxide is formed by dissolving the quaternary ammonium halide or hydrogen sulfate in water, and subjecting the solution to electrolysis until 0.5 mole equivalents of the free halogen or oxygen gas has been formed.

Preferably, the strong acid is concentrated sulfuric acid, and the metal halide is sodium chloride.

In another preferred embodiment, the invention comprises quaternary ammonium salts consisting of one or more different sized benzylkonium molecules ranging in size from $C_{12}$ to $C_{18}$. Preferred benzylkonium molecules include alkyl dimethyl benzyl ammonium chloride (benzalkonium chloride) 60 weight % $C_{14}$, 30 weight % $C_{16}$, 5 weight % C18 and 5 weight % $C_{12}$.

A stock solution may be prepared comprising of about 500,000 ppm of quaternary ammonium salt molecules. In another preferred embodiment, the stock solution may be comprised of about 50 weight percent quaternary ammonium salt molecules. The stock solution may be diluted to a concentration of 10,000 to 25,000 ppm for application with tap water.

The invention further comprises a method for applying quaternary ammonium salts to the paper face of assembled wallboard. In a preferred embodiment of this method, the quaternary ammonium salt may be applied to the paper face of assembled wallboard just before the wallboard enters the kiln for drying using a spray bar apparatus. In a preferred embodiment, the amount of solution applied will be between 0.25 to 4% of the weight of the dry paper per wallboard face. Preferred concentrations of active quaternary ammonium salts range from 4 to 20 mg/square foot of wallboard paper. In a particularly preferred embodiment, the amount of the concentration of active quaternary ammonium salts ranged from about 6 to 14 mg/square foot, most preferably between about 10 to 12 mg/square foot. A preferred method includes applying the quaternary ammonium salt laterally across the wallboard sheet at a line speed of 400-500 feet per minute.

Another embodiment of the invention may comprise a material into which a quaternary salt is blended or integrated, such that molds, algae, and other microbes will not grow on the material. The material may comprise a polymer or other solid. In a preferred embodiment, quaternary ammonium salt is blended with water, preferably with a motorized metal mixing device. Then calcium aluminosilicate, preferably with a particle size of >300 microns, is added, and the mixture is blended to form a thick slurry. The slurry may then be poured out onto a surface, preferably aluminum foil on the floor of a laboratory, where it is allowed to dry for approximately two weeks. Finally, dry lumps of calcium aluminosilicate are aggregated and placed in an 80 degree centigrade incubator for about 1 week to dry further.

In a preferred embodiment, lumps and powdered matrix may be ground and jet milled to achieve an approximate particle size of 5 microns or less. Quaternary ammonium salt coated aluminosilicate particles may then be blended with vinyl and other types of polymers and formed into rolled or extruded rigid high-impact films.

In a further preferred embodiment, a quaternary ammonium salt as described may be used to confer flexibility to rigid high-impact plastic when incorporated into the structure of the plastic.

Example 1

Evaluation of the Anti-Mold Properties of a Quaternary Ammonium Salt Prepared Using Cetyl Dimethylamine and 3-Chloro-1-Propanol Ten grams of 3-chloro-1-propanol (Aldrich, St. Louis, Mo.) was placed in a flask with 10 g of N,N-dimethylhexadecylamine or cetyl dimethylamine (Fluka, Buchs, Switzerland). The flask was stoppered, and the reagents were allowed to react overnight at 68.6° C.

To determine the effective anti-mold level and whether the quaternary ammonium salt would effectively bind and remain resident on paper the solution manufactured as described above was diluted as follows before application to strips of paper:

A. 5 ml of Quat solution plus 30 ml of anhydrous ethyl acetate (Sigma, St. Louis, Mo.) plus 5 ml of 70% isopropanol (Sigma)

B. 1 ml of Quat plus 30 ml of anhydrous ethyl acetate (Sigma) plus 5 ml of 70% isopropanol (Sigma)

C. 0.5 ml of Quat plus 30 ml of anhydrous ethyl acetate (Sigma) plus 5 ml of 70% isopropanol (Sigma)

D. 0.1 ml of Quat plus 30 ml of anhydrous ethyl acetate (Sigma) plus 5 ml of 70% isopropanol (Sigma)

E. 0.05 ml of Quat plus 30 ml of anhydrous ethyl acetate (Sigma) plus 5 ml of 70% isopropanol (Sigma)

F. 0.01 of Quat plus 30 ml of anhydrous ethyl acetate (Sigma) plus 5 ml of 70% isopropanol (Sigma)

After dilution, solutions A-F were each applied to 1.2 cm×28 cm strips of high porosity white filter paper (Whatman Grade 222, Middlesex, UK). One paper strip each was dipped in solutions A-F such that each strip was totally saturated. Control strips were dipped in deionized water for control purposes. After treatment all paper strips were placed on sheets of aluminum foil and dried at 68.6° C. to remove any excess ethyl acetate/water. After drying, paper strips were suspended vertically with the lower end being immersed in deionized water (about 50 ml) to a depth of about 1 cm. Diffusion of water up the paper by capillary action was then carried out for about 20 hr. The objective of this step was to determine whether exposure to water would effectively mobilize the quaternary ammonium salt and thereby render the treatment ineffective with respect to mold inhibition. After the chromatographic step, the waterfront was marked and the pieces were again transferred to a 68.6° C. incubator to dry.

Strips treated with solutions A-F were designated 1-6, respectively. Control strips were designated "C". The effect of treatment on the chromatographic properties of the paper strips is presented in Table 1 below.

TABLE 1

Effect of Treatment of Paper on Chromatographic Properties

| Strip Designation | Treatment Solution | Chromatography Pattern |
| --- | --- | --- |
| 1 | A | Water only moved up the strip about 4 cm |
| 2 | B | Water moved up the strip about 25 cm |
| 3 | C | Water moved up the strip about 25 cm |
| 4 | D | Water moved up the strip about 25 cm |
| 5 | E | Water moved up the strip about 25 cm |
| 6 | F | Water moved up the strip about 25 cm |
| C | Control | Water moved up the strip about 25 cm |

Paper pieces (1×1 cm) were excised from strips 2-6, at about 4 cm from the origin, or the end of the strip initially exposed to water. These pieces were designated 2-6. For Strip 1, as noted in Table 1 above, the mobile phase only diffused up the strip to a height of about 4 cm. Taking this into consideration, paper pieces were excised at about 2 cm from the origin and at about 2 cm above the diffusion wetting end point (the waterfront), which is about 6 cm from the origin. The pieces were designated 1A and 1B, respectively. Control pieces were excised from the control strips at about 4 cm above the origin and designated "C".

Anti-mold and dosage effects of treatment with the Quat solutions were determined by culturing treated and untreated paper samples that were inoculated with mold spores. Specifically, a plate containing agar medium (325 malt agar, Blakelee's Formula) was inoculated with *Aspergillus fumigatus* and cultured at 30° C. for about 2 weeks. By this time spore formation had occurred. Spores for paper inoculation were collected by gently rinsing the plate with water. This process in addition to producing a spore suspension also removed the fungal conidiophore structures and hyphae. Conidiophore and hyphae structures were removed by filtering the suspension through sterile cotton. All paper pieces were then inoculated with spores by dipping treated and control pieces of paper in the spore suspension.

Mold resistance was determined by two distinct processes, designated Procedure #1 and #2. Procedure #1 was used to determine whether spores would germinate and mold would grow on treated paper and the effective anti-mold dose, i.e. the dilution that was effective in suppressing mold growth. Procedure #2 was designed to determine whether the quaternary ammonium salt was effectively bound to the paper or extracted from the treated paper under exposure to aqueous conditions. Extraction would effectively render the treatment ineffective at some point, i.e., extraction could potentially reduce the anti-microbial level below an effective threshold level or dose.

For Procedure #1, paper pieces (1A, 1B and 2-6) obtained as described above were inoculated and placed on a sterile culture plate having an agar layer of culture medium. A control piece (C), likewise, was inoculated and placed on the same culture plate. Plates were then transferred to a 30° C. incubator for five days at which time control mold growth was readily evident.

To address the extraction issue, Procedure #2 was carried out. Culture plates were evenly inoculated with *Aspergillus fumigatus* spores. Treated pieces 1A and 2-6, respectively, were each placed on an inoculated plate. Control pieces were likewise inoculated and a piece was also placed on each culture plate with a treated piece. Plates were then transferred to a 30° C. incubator for five days at which time control mold growth was readily evident. A visual inspection of the control plates showed that mold was completely inhibited on papers 1A, 2, 3 and 4, while mold growth occurred on paper excised from strips 5 and 6, i.e., paper treated with Solution E and F. As would be expected mold grew on all the control pieces (C), i.e., paper that was not treated. Effectively a 1:300 dilution of the quaternary salt solution was totally effective at inhibiting mold replication. No growth of mold was seen in piece D, treated with Solution 4, having an effective dilution of 1:300 of the Quat salt. By contrast, the outgrowth of mold hyphae was clearly evident from the control (C) piece of paper.

Using Procedure #2, it was seen that mold grew on all the "C" pieces, whereas no mold growth was evident on any of the treated pieces. This procedure was different from Procedure #3 in that mold growth only occurred if the paper became contaminated with spores from the plate or if mold grew through the paper. It was also seen that there was some diffusion of the Quat salt into the agar particularly at the higher concentrations of the applied Quat salt resulting in a zone of inhibition around the treated paper, and particularly around pieces 1A, 2, and 3. However, the amount of diffusion was minimal even for paper strips treated with a 1:35 and 1:70 dilution of the original Quat salt stock solution. No diffusion was evident for paper treated with a 1:300 dilution (piece 4) of the original Quat salt solution, which was the minimal concentration shown to inhibit mold growth.

It is important to determine the amount of diffusion because any anti-mold agent must remain resident because of the potential for multiple rounds of water exposure. Were the anti-mold agent to rapidly diffuse by capillary action across the paper then the antimicrobial could reach ineffective concentrations. This effect can be seen in the commercially available Microban® product (Microban International, Ltd., New York, N.Y.), which diffuses rapidly out of treated paper causing a large zone of inhibition. Use of the Microban product on gypsum panels, namely SHEETROCK® Brand gypsum panels (USG Corporation, Chicago. Ill.) is described in U.S. Pat. No. 6,767,647. The Microban® product failed when applied in a production plant environment because the anti-mold components comprised propconazole, sodium pyrithione, tolyl diiodomethyl sulfone, tebuconazole, thiabendazole, 3-iodo-2-propynyl butylcarbamate, and mixtures thereof, which are susceptible to extreme heat such as might be present transiently in a gypsum board manufacturing plant, i.e., elevated temperatures as high as 690° F. The higher molecular weight Quat salts, such as those used herein can take such temperatures and remain functional.

Example 2

Preparation of a Quaternary Ammonium Salt from Tallow Amine and Determination of the Anti-Mold Properties when Applied to Paper Manufactured into Wallboard To prepare the quaternary ammonium salt compounds, 20 kg of 2-chloro ethanol (Sigma) was placed in a vessel. 27 kg of tallow amine (Tomah Products, Inc., Milton. Wis.) was heated to 68.6° C. and slowly blended with the 2-chloroethanol. The mixture was incubated at 80° C. for 48 hrs. 57 kg of quaternary ammonium salt mixture was blended with water at a ratio of about 1:40 wt/wt to yield about 1000 kg of a quaternary ammonium salt solution.

Two distinct processes were used to culture for mold and mold inhibition. Procedure 1 was used to determine whether spores would germinate and grow on treated paper. Procedure 2 was designed to determine whether the diluted quaternary ammonium salt solution would diffuse from the paper and/or prevent mold growth on the paper. For both procedures, 3 MM paper samples (1.5 cm×1.5 cm) were immersed in the quaternary salt solution and dried at 80° C. Paper control pieces were dipped in water and likewise dried. In Procedure 1, treated and control papers were inoculated with mold spores. Inoculated paper pieces were each placed on a sterile culture plate having an agar layer of culture medium. Plates were then transferred to a 30° C. incubator for five days. In Procedure 2, plates were evenly inoculated with *Aspergillus fumigatus* spores. Treated and control pieces were placed on an inoculated plate. Plates were transferred to a 30° C. incubator for five days.

Mold growth was detected on the control paper inoculated with mold spores while there was no detectable mold growth on paper pieces treated with the 1:40 dilution of the original quaternary ammonium salt solution. Hyphae growth from the control paper was readily evident by 24 hr post-incubation. Using Procedure 2 it could be seen that there was a zone of inhibition around the paper treated with the diluted quaternary ammonium salt solution whereas mold grew up to and over the edges of the control paper. The zone of inhibition was small, indicating the quaternary ammonium salt did not readily diffuse from the paper. Together these results indicated that a 1:40 dilution of the quaternary salt solution produced by reacting a tallow amine with 2-chloroethanol was an effective biocide that inhibited mold growth on paper.

To test the effects of the quaternary ammonium salt compounds on wallboard paper, a roll of 50.25 inch wide 42 lb two pound Cream Face wallboard paper, manufactured by Republic Paper (Lawton, Okla.) from recycled cardboard and newspaper was shipped to Corrugated Services, Inc. (Forney, Tex.) along with 1000 kg of diluted quaternary ammonium salt prepared as described above. Sequential six thousand linear foot sections of the roll were coated at 2, 5 and 8 lb per 1000 sq ft with the quaternary ammonium salt solution. A slight amber color was imparted to the paper at the higher doses without a noticeable change in brightness. A standard Cobb test for this type of paper has a value of 26 g/m$^2$, which is a measurement of how much water is absorbed. The Cobb values for the treated papers was 75, 87 and 102 respectively, i.e., the treated papers held more water.

Cream face wallboard paper coated as described above was shipped from Corrugated Services, Inc. to an American Gypsum plant located in Duke, Okla. The paper roll was mounted on the manufacturing line and 6000 ft successive sections of the roll were manufactured into wallboard. No physical changes were noted other than a slight change in the coloration due to the coating as noted above. It was also noted that the Cobb values increased in a direct relation to the amount of quaternary ammonium salt applied to the paper. It was concluded that the noted changes would not in anyway potentially interfere in the usefulness or sale of the product. Wallboard was manufactured from portions of the paper roll coated with 2, 5 and 8 lb per 1000 sq ft, respectively. The wallboards manufactured in succession from the coated paper were designated A, B and C. Wallboard manufactured using uncoated cream face paper was designated D.

Each specimen was shipped to an independent test laboratory for the ASTM D 3273 test, i.e., the mold resistance test, and each was labeled with coded dosing rate, i.e., A, B, C or D, on the back side. In addition, each specimen was given a number per localized position on the wallboard sheet (see FIG. 1) and the location number was written on the back side of each specimen. Samples for each dosing level were obtained from one of three different production wallboard sheets. Samples for each dose were obtained proximal to the knife-cut end. All ASTM D 3273 specimens for each dose were prepared from a single sheet of board. Samples were submitted to three different test laboratories for mold resistance ASTM D3273 validation tests: DL Labs (Brooklyn, N.Y.), Micro Star Lab Limited (Crystal Lake, Ill.), and Northeast Laboratories. Inc. (Berlin, Conn.). All samples prepared were 3"×4". Samples tested by each laboratory were numbers 1-3, 7-9 and 14-16 for each dosing level.

1. DL Labs Report

A. Objective

To determine the fungal resistance of four sets of submitted coated panels.

B. Products Tested

Coated test panels and an uncoated control were submitted for testing. The coatings were identified as follows:

Sample A: Formulation MC-615 2 lbs. wet wt.

Sample B: Formulation MC-615 5 lbs. wet wt.

Sample C: Formulation MC-615 8 lbs. wet wt.

Sample D: Control

C. Procedures

The fungal resistance of the coated specimens was conducted in accordance with procedures outlined in:

ASTM D 3273, "Standard Test Method for Resistance to Growth of Mold on the Surface of Interior Coatings in an Environmental Chamber."

ASTM D 3274, "Standard Test Method for Evaluating Degree of Surface Disfigurement of Paint Films by Microbial (Fungal or Algal) Growth or Soil and Dirt Accumulation."

In addition, uncoated test article panels were exposed in the Mildew Chamber as a control.

D. Results

The mold and mildew resistance was rated using a scale of 10 to 0, as determined by comparison with pictorial standards depicted in ASTM D 3274. The ASTM ratings are as follows in Table 2 below:

TABLE 2

| Rating | Fungal Growth |
| --- | --- |
| 10 | No fungal growth |
| 9 | Trace of fungal growth |
| 8 | Very slight fungal growth |
| 6 | Slight fungal growth |
| 4 | Moderate fungal growth |
| 2 | Considerable fungal growth |
| 0 | Severe fungal growth |

The MC-615 coated wallboard test panels exhibited the resistances to fungal growth after 28-days of exposure in the mold/mildew chamber shown in Table 3 below.

TABLE 3

| Sample | Rating |
| --- | --- |
| A | 10 |
| B | 9 |
| C | 9 |
| D | 6-8 |
| Control | 4 |

2. Micro Star Lab Limited Report

A. Objective

To determine if the wallboard samples submitted for testing demonstrate mold-resistance against the fungi used in the ASTM D3273 test. Upon request, the samples were incubated for an additional 2 weeks. That additional data and observations were added to the original report and are shown here in BOLD print.

B. Product Tested

Four wallboard samples with 5 replicates each were submitted for ASTM D3273 testing. These samples were identified as having the following treatment schemes shown in Table 4.

TABLE 4

| Sample | Treatment |
| --- | --- |
| Sample A-1, A-5, A-8, A-12, A-16 | Formulation MC-615 @ 2 lbs. wet weight |
| Sample B-1, B-5, B-8, B-12, B-16 | Formulation MC-615 @ 5 lbs. wet weight |
| Sample C-1, C-5, C-8, C-12, C-16 | Formulation MC-615 @ 8 lbs. wet weight |
| Sample D-1, D-5, D-8, D-12, D-16 | Untreated control |

C. Procedure 3 weeks prior to testing, fresh soil was seeded with fungal spores of *Aspergillus niger* ATCC 6275, *Penicillium citrinum* ATCC 9849, and *Aureobasidium pullulans* ATCC 9348 and allowed to grow in the humidified chamber at 30° C. After 2 weeks, exposed PDA (potato dextrose agar) plates were placed in the chamber for 30 minutes to determine that fungal spores were being produced by the fungi seeded into the soil. After confirmation of fungal sporulation, prepared paper samples were hung in the D3273 chamber. Untreated wallboard pieces were also hung as additional controls. The chamber used for the test samples were heated by heating elements submerged in water, so the flat lid of the chamber did not experience condensation like those chambers held at room temperature. The plate glass lid provided an adequate seal so that a 98-99% relative humidity was maintained during the test. The use of a glass aquarium as a test chamber allowed for casual observation without opening the chamber.

Samples were examined weekly for fungal growth. Test samples were spread out in a tissue culture hood in preparation for reading. The samples were rated according to the ASTM D3273 grading scale shown in Table 5 below.

TABLE 5

ASTM D3273 Grading Scale

| Rating | Definition |
| --- | --- |
| 10 | no growth |
| 9 | 90% clear (10% or less of surface covered with growth) |
| 8 | 80% clear (20% of surface covered with growth) |
| 7 | 70% clear (30% of surface covered with growth) |
| 6 | 60% clear (40% of surface covered with growth) |
| 5 | 50% clear (50% of surface covered with growth) |
| 4 | 40% clear (60% of surface covered with growth) |
| 3 | 30% clear (70% of surface covered with growth) |
| 2 | 20% clear (80% of surface covered with growth) |
| 1 | 10% clear (90% of surface covered with growth) |
| 0 | 0% clear (100% of surface covered with growth) |

D. Results

The generic controls were clearly darkened with fungal growth after two weeks. This growth appeared about one week earlier than the growth on the treated samples, also demonstrating more color from more mature conidia. Gross observation showed little change in the treated samples. A magnification of one of the control samples (D-12) showed that, although the mold growing had not changed color, it was still visible with the aid of a lighted magnifier. Stereoscopic examination showed heavy amounts of fungal filaments spreading across the surface. About 70% of the fields showed fungal involvement. The back side of a treated sample (A-8) showed moderately heavy growth with a 2× lighted magnifier. Due to the immaturity of the growth, the fungi did not show any coloration, making them difficult to see. Additional incubation would likely allow the growth to become heavier and easier to see with the naked eye. Sample C-12 was rated an "8" although no fungal growth was visible, even with the 2× lighted magnifier. Growth was only evident using the stereoscope at 20×. Photomicrographs of images seen under the stereoscope are of poor quality since the picture is only 2-dimensional. Normal viewing through a stereoscope presents a 3-dimensional image.

There was variability between the 5 replicates for each group, even the untreated control samples. The generic controls used by the lab did not show this variability. These generic controls were spaced at both ends and the middle of the chamber to ensure that the indirect inoculation of fungal spores coming off of the moldy soil was viable and as uniform as possible. The growth seen on these generic controls is typical of other D3273 chambers used at the lab. Each customer's samples were incubated in their own chamber so contamination from one customer's samples to another could not occur.

No fungal growth appeared on any of the submitted wallboard samples until the 3-week reading. Since growth on the generic wallboard controls showed growth after 2 weeks, it appeared that all of the treated samples were less susceptible to fungal growth than the bargain untreated wallboard.

3. Northeast Laboratories, Inc. Report

Samples of wallboard were prepared for testing according to the ASTM D-3273 method, as described in the Micro Star Lab report and Table 4 above. The results were measured after 28 days, with "0" being equal to no mold resistance and "10" being equal to complete mold resistance. Results are shown in Table 6 below.

TABLE 6

| Wallboard Description | Sample Rating | | | | |
|---|---|---|---|---|---|
| | Sample #1 | Sample #5 | Sample #8 | Sample #12 | Sample #16 |
| A-Front | 7 | 6 | 10 | 9 | 9 |
| A-Back | 3 | 6 | 5 | 5 | 2 |
| B-Front | 10 | 10 | 10 | 10 | 6 |
| B-Back | 10 | 10 | 10 | 5 | 5 |
| C-Front | 7 | 10 | 10 | 10 | 10 |
| C-Back | 2 | 4 | 6 | 6 | 9 |
| D-Front | 5 | 7 | 8 | 6 | 7 |
| D-Back | 5 | 8 | 7 | 6 | 4 |

Example 3

Preparation of Quaternary Ammonium Salt Compounds Using a Process Whereby the Quaternary Ammonium Salt is Generated Using Chloride Ion-Promoted Alkylation of a Tertiary Amine, Possible by Generating the Chlorohydrin In Situ In Examples 1-2, the halogenated alcohol was reacted with an amine to generate a quaternary ammonium salt. Halogenated alcohols are costly and they have significant associated negatives, i.e., they are in general rather toxic. Specifically, with respect to 2-chloroethanol or ethyl chlorohydrin, it is very expensive, it is a blistering agent and an oral lethal dose in humans is 50-500 mg/kg. Therefore, alternative and cheaper methods were derived to construct desirable quaternary ammonium salts for the biocidal applications described herein. Quaternary ammonium salts were prepared from chemically defined pure amines and a mixture (tallow amines). The effect of alcohol chain length on the melting point and water solubility of the quaternary ammonium salts synthesized were evaluated as well as anti-mold properties.

1. Preparation

Nine quaternary ammonium salt compounds were prepared using the components listed in Table 7 below.

TABLE 7

| Solution 1 | 6.2 g ethylene glycol |
| | 4.9 g sulfuric acid |
| | 5 mL water |
| | 5.85 g sodium chloride |
| | 18.5 g N,N-dimethyldecylamine |
| Solution 2 | 10.6 g diethylene glycol |
| | 4.9 g sulfuric acid |
| | 5 mL water |
| | 5.85 g sodium chloride |
| | 24.1 g N,N-dimethyldecylamine |
| Solution 3 | 10.6 g triethylene glycol |
| | 4.9 g sulfuric acid |
| | 5 mL water |
| | 5.85 g sodium chloride |
| | 24.1 g N,N-dimethyldecylamine |
| Solution 4 | 6.2 g ethylene glycol |
| | 4.9 g sulfuric acid |
| | 5 mL water |
| | 5.85 g sodium chloride |
| | 24.2 g N,N-dimethyltetradecylamine |
| Solution 5 | 6.2 g ethylene glycol |
| | 4.9 g sulfuric acid |
| | 5 mL water |
| | 5.85 g sodium chloride |
| | 11.3 g N,N-dimethylcyclohexylamine |
| Solution 6 | 18.6 g ethylene glycol |
| | 4.9 g sulfuric acid |
| | 5 mL water |
| | 5.85 g sodium chloride |
| | 24.1 alkyl amine (tallow amine) |
| Solution 7 | 6.2 g ethylene glycol |
| | 4.9 g sulfuric acid |
| | 5 mL water |
| | 5.85 g sodium chloride |
| | 28.3 g N,N-dimethyl-1-octadecylamine-tertiary amine |
| Solution 8 | 10.6 g diethylene glycol |
| | 4.9 g sulfuric acid |
| | 5 mL water |
| | 5.85 g sodium chloride |
| | 28.3 g N,N-dimethyl-1-octadecylamine-tertiary amine |
| Solution 9 | 15.9 g triethylene glycol |
| | 4.9 g sulfuric acid |
| | 5 mL water |
| | 5.85 g sodium chloride |
| | 28.3 g N,N-dimethyl-1-octadecylamine-tertiary amine |

For each solution, the glycol portion used in the synthesis of the quaternary ammonium salt was first cooled to 4° C. Likewise, the sulfuric acid portion was also cooled to 4° C. After cooling, the sulfuric acid was slowly blended with the glycol while stirring. Following this step, 5 mL of water was added to the mixture followed by the addition of 5.85 g sodium chloride. The mixture was then heated and stirred until the sodium chloride was dissolved.

Several of the amines used in the preparation of the quaternary ammonium salts are solids at room temperature, such as alkyl amine and N,N-dimethyl-1-octadecylamine. Therefore, the amount of each amine to be added to each solution was first weighed out and then heated to a liquid state. The liquid amine was in each case then added to the mixture prepared as described above and as listed in Table 1. After all of the components were mixed together, the solutions were stirred briefly and then incubated at 80° C. for 24 hours.

This method produces a solution containing equal amounts of the quaternary ammonium cation, chloride anion, the hydrogen sulfate anion, and sodium cation. It is chemically equivalent to a 1:1 mixture of the quaternary ammonium chloride and sodium hydrogen sulfate, or a 1:1 mixture of the quaternary ammonium hydrogen sulfate and sodium chloride, or a 1:1 mixture of each of these two mixtures.

After incubation, it was noted that several of the quaternary ammonium salt compounds were found to have vastly different solution viscosities. In general, the solutions of quaternary ammonium salts prepared using di- or triethylene glycol had lower viscosities. Only the quaternary ammonium salts prepared using Solutions 5 and 6 were liquid at room temperature.

2. Determination of Water Solubility

Most quaternary ammonium salts dissolve readily in water. The quaternary ammonium salts prepared in Example 1 in general are rather large due to their large alkyl components. To test the efficacy of the synthetic procedure, one gram of each quaternary ammonium salt prepared using the formulas for Solutions 1-12 above was weighed out. Water was then added to each quaternary ammonium salt sample. The water and quaternary ammonium salts were then heated to near boiling. Each sample was then stirred and a determination as to whether the quaternary ammonium salt was soluble in water was made. The quaternary ammonium salts prepared using the formulas for Solutions 1-3 and 10-12 were soluble at elevated temperatures but became insoluble at room temperature. The quaternary ammonium salts prepared using the formulas for Solutions 4-9 readily dissolved and maintained their solubility at room temperature. Based on these results it appeared probably that the protocols described in Example 1 were effective in the synthesis of quaternary ammonium salts.

3. Mold-Resistant Properties of the Quaternary Ammonium Salts

Dilutions (1:20) of each of the formulas for Solutions 1-12 above were prepared. Pieces of 1 cm×1 cm filter paper (Whatman, Brentford, UK) were dipped into each solution and then dried in an 80° C. incubator. Control pieces of filter paper were prepared that were not treated with any of the solutions.

In Test 1, the treated and control paper samples were then inoculated with a spore/vegetative suspension of *Aspergillus fumigatus* (ATCC1022). The inoculated pieces of paper were then placed on the surface of Malt Extract agar culture medium (ATCC Medium 325) in a Petri plate. Petri dishes were then incubated at 30° C. for at least 48-72 hours.

In a separate test, Test 2, both treated and control paper pieces were placed on the surface of Malt Extract agar medium in a Petri plate in which the surface of the agar had been inoculated with a spore/negative suspension of *Aspergillus fumigatus* to produce a mold lawn. The Petri dishes were then incubated at 30° C. for about 48 to 72 hours. The objective of this study was to determine whether the quaternary ammonium salt remained associated with the saturated paper or whether it readily diffused across the surface of the inoculated agar. The test also indicated whether the solution used to treat the paper was in fact biocidal to the mold.

Solutions 1-9 were all shown to be biocidal using the Test 1 protocol. However, there were differences amongst the solutions. Solutions 6-9 were minimally effective. While N,N-dimethyl-1-octadecylamine was converted into quaternary ammonium salts, the effectiveness of the six formulations tested was only marginally increased when triethylene glycol was used in the synthesis procedure. The derived quaternary ammonium salts were very slightly soluble at room temperature and likely would not be effective at disrupting the membrane of the vegetative *Aspergillus fumigatus* organism.

Solutions 4, 5, 6, and 7 all readily dissolved and were very biocidal. In addition, they all diffused across the surface of the inoculated agar. Due to their solubility and their capacity to readily diffuse, it is likely that these compounds have little utility for application to the surface of wallboard paper. They will likely diffuse away from the surface exposed to water.

The quaternary ammonium salt produced using the formula for Solution 8 appeared to have the most desirable characteristics. It did not readily diffuse but had strong biocidal properties. However, although this solution is desirable, the cost of obtaining the raw materials for preparation of the product and the amount to be applied to the paper must be taken into consideration.

By contrast, the raw materials used to formulate Solution 9 are readily available at cost effective prices. Ethylene glycol, sodium chloride, and sulfuric acid are available at commodity prices. Alkyl tallow amines are available from a number of sources and ideally they contain alkyl chain lengths of $C_{16}$ and $C_{18}$. Amines of this length when converted to quaternary ammonium salts can be converted to liquid at 80° C. and when diluted with water form highly biocidal solutions. Moreover, the quaternary ammonium salts produced using the components described in Solution 9 do not readily diffuse when they are dried onto a matrix such as paper. They effectively hydrogen bond to the paper, forming numerous stable attachment points. Furthermore, the biocidal effectiveness of Solution 9 is maintained even at high dilutions. Dilutions of 1:40 and 1:80 still produce biocidal effects.

In Example 2, it was clearly shown that quaternary ammonium salts derived from the reaction of tallow amines (alkyl amines) with 2-chloroethanol are highly biocidal.

As demonstrated in Example 3, a chloride ion-promoted process whereby the chlorohydrin may be, in principle, generated in situ, is equally effective in the generation of quaternary ammonium salts as the direct reaction between a tertiary amine and the chlorohydrin. Specifically, one may suggest that the chloride anion reacts with ethylene glycol in sulfuric acid solution yielding 2-chloroethanol that then undergoes reaction with the tallow amines to yield a highly biocidal solution of quaternary ammonium salts (chlorides and hydrogen sulfates). This simple rationalization explains the role of the chloride ion, which dramatically increases the rate of the reaction between the tertiary amine and the glycol in sulfuric acid solution. The whole process takes place in a single vessel without additional steps, thereby facilitating manufacturing.

Example 4

Preparation of a Quaternary Ammonium Salt Using a Blend of Three Alkyl Amines

1. Preparation

Two different batches of quaternary ammonium salts were prepared using the components listed in Table 8 below.

TABLE 8

| Formula A | 244 g Ethylene glycol |
| --- | --- |
| | 196 g Sulfuric acid |
| | 400 g Water |
| | 234 g Sodium chloride |
| | 396.2 g AT-1495 (alkyldimethyl amine C-14) |
| | 452.8 g AT-1695 (alkyldimethyl amine C-16) |
| | 283 g AT-1895A (alkyldimethyl amine C-18) |
| Formula B | 244 g Ethylene glycol |
| | 196 g Sulfuric acid |
| | 400 g Water |
| | 234 g Sodium chloride |
| | 283 g AT-1495 (alkyldimethyl amine C-14) |
| | 566 g AT-1695 (alkyldimethyl amine C-16) |
| | 283 g AT-1895A (alkyldimethyl amine C-18) |

Amines were obtained from Proctor and Gamble (Kansas City, Mo.). For each formula, amines were weighed out separately and blended together in a reaction vessel. After mixing by stirring the amine blend was heated to about 90° C., then ethylene glycol was added to each blend while stirring. Separately for each formula, salt was added to 200 g water to form a suspension. The salt suspensions were then individually added to the contents of the Formula A and Formula B reaction vessels while stirring.

To formally generate the chlorohydrin in situ, sulfuric acid for each formula was first mixed with 200 mL of water. Then for each reaction, the sulfuric acid was slowly added to each reaction vessel in about 25 mL increments. The reaction is highly exothermic and if the acid is added too rapidly, a violent reaction will occur resulting in loss of product by splattering and boiling over of the reaction vessel contents.

As the sulfuric acid was added, the solution became highly viscous. As might be expected, the viscosity of Formula B was somewhat higher than that of Formula A. Nevertheless, for both formulas, the product had to be vigorously scraped from the side of each vessel. The temperature of the reactants at that point was greater than 100° C. To reduce the viscosity of the end product, all reactants were converted into a suspension by the addition of about 800 mL of water. After the formation of a suspension of all contents while heating at about 90° C. the product was ready for use. The viscosity of the products as described above and the difficulty of suspending the quaternary ammonium salt mixtures, i.e. Formula A and Formula B, necessitated further evaluation of the process. It was found that if the amines were blended with an additional 400 g of water first, this would lower the viscosity of the overall product without seeming to diminish the product yield.

2. Mold-Resistant Properties of the Quaternary Ammonium Salts

The mold-resistant properties of Formulas A and B were tested essentially as described in Example 3 above, except each of the products produced as described above were diluted 1:80 before application to paper. Both Formula A and Formula B were found to inhibit mold growth on paper. In addition, they were readily dispersed in water as would be expected for a quaternary salt.

Formula B was somewhat easier to dissolve because the quaternary amine salt blend contained a greater composition of short chain alkyl salts, i.e., it contained more quaternary salt molecules derived from AT-1495 (alkyldimethyl amine C-14). Therefore, it was decided to carry out a full evaluation of the anti-mold properties by coating wallboard paper and carrying out the ASTM 3273 method and grading scale for anti-mold evaluation.

With this in mind, a 1:40 dilution of the product was applied to wallboard paper at a calculated concentration of 25.2 μg and 63.6 μg per sq ft. Likewise, a 1:80 dilution of the product was applied to wallboard paper at a calculated concentration of 12.6 μg and 31.9 μg per sq ft. The coated paper was subsequently converted into wallboard as described in Example 2 above. In addition, 3×4 pieces of wallboard were extracted and sent to Northeast Laboratories, Inc., 129 Mill Street, Berlin, Conn. 06037-9990, for mold challenge using the ASTM 3273 method.

After four weeks, no fungal growth was observed on the test articles, labeled Articles 1-8. Fungal growth was rated using the scale of 10 to 0 using the ASTM D3274 pictorial standard as well as with the stereo-microscope at 20×. The ASTM D3274 ratings are shown in Table 2 above. The correlation of the rating with the amount of quaternary ammonium salt applied to paper are shown in Table 9 below.

TABLE 9

| Sample | Rating | Amount (μg/sq ft) of quat salt |
|---|---|---|
| Article 1 | 4 | 12.6 |
| Article 2 | 10 | 12.6 |
| Article 3 | 10 | 31.9 |
| Article 4 | 10 | 31.9 |
| Article 5 | 10 | 25.2 |
| Article 6 | 10 | 25.2 |
| Article 7 | 10 | 63.6 |
| Article 8 | 10 | 63.6 |
| Control | 0 | — |

This study showed Formula A when applied to wallboard paper was effective in preventing mold formation at concentrations greater than 25.2 μg per sq ft.

Example 5

Preparation of Quaternary Ammonium Salts by Chloride Ion Promoted Animation of Benzyl Alcohol As demonstrated in Examples 2-4 above, quaternary ammonium salts can be readily synthesized using a process whereby a chlorohydrin is formally generated in situ from dihydroxy alcohols of different lengths. As an extension of the effectiveness of this process, a monohydric alcohol alcohol, e.g. benzyl alcohol, can be used as well. Specifically, a blend of quaternary ammonium salts was prepared using the components listed in Table 10 below.

TABLE 10

| Formula C | 80 g Benzyl alcohol |
|---|---|
| | 40 g Sulfuric acid |
| | 432 g Water |
| | 48 g Sodium chloride |
| | 10 g AT-1295 (alkyldimethyl amine C-12) [5%] |
| | 120 g AT-1495 (alkyldimethyl amine C-14) [60%] |
| | 60 g AT-1695 (alkyldimethyl amine C-16) [30%] |
| | 10 g AT-1895A (alkyldimethyl amine C-18) [5%] |

The amines were initially blended together and the other components were added as described in Example 4 above. A major difference was noted in the product produced. The viscosity was substantially less.

As described in previous examples, the quaternary ammonium salt was effective at preventing mold growth when the blend was diluted and applied to Whatman paper. Further analysis showed a concentration of 500 ppm was very effective at preventing mold growth when applied to wallboard paper and evaluated using the ASTM 3273 method described above. At higher concentrations of Formula C it was difficult to coat the paper because of the very high surfactant properties. The liquid phase caused penetration of the paper fiber very rapidly. Effectively, the water update was much more than desired and therefore a great deal of additional product would have to be added to totally coat the paper surface than would be desirable from an economic viewpoint. The dilution scales and amount of product per surface area are shown in Table 11 below.

TABLE 11

| Concentration as Applied (ppm) | mg/g | Stock Dilution | mg/ft$^2$ | ppm/ft$^2$ |
|---|---|---|---|---|
| 5000 | 5 | 1:10 | 3.8 | 200 |
| 4000 | 4 | 1:12.5 | 3.04 | 160 |
| 3000 | 3 | 1:16.7 | 2.28 | 120 |
| 2000 | 2 | 1:25 | 1.52 | 80 |
| 1500 | 1.5 | 1:33 | 1.14 | 60 |
| 1000 | 1 | 1:50 | 0.76 | 40 |
| 500 | 0.5 | 1:100 | 0.38 | 20 |
| 400 | 0.4 | 1:125 | 0.31 | 16 |
| 300 | 0.3 | 1:166 | 0.23 | 12 |
| 200 | 0.2 | 1:250 | 0.15 | 8 |
| 100 | 0.1 | 1:500 | 0.076 | 4 |
| 50 | 0.05 | 1:1000 | 0.038 | 2 |

The workable range of product concentration appears to be between 50 ppm and 200 ppm per square foot of wallboard paper, but the most probable range is between 20 ppm and 40 ppm per square foot of wallboard paper.

Example 6

Quaternary Ammonium Salt Applied to Clay

A sample prepared according to the formula for Solution 9 was diluted to a 1:15 dilution by adding 20 g of the sample to 280 g of water. This mixture was then heated to evenly disburse the salt at 80° C. 100 g of kaolin clay (Engelhard Corporation, Iselin, N.J.) was added and evenly disbursed. This mixture was then heated for about 24 hours at 80° C. to remove water. The dried kaolin clay salt mixture was broken up using physical hammering with a mortar. Contact was not excessive and a rather even clay material was produced.

To determine the biocidal effect of this clay material, a lawn of *Aspergillus fumigatus* was produced by streaking a spore/vegetative suspension onto agar in a Petri dish. After inoculation, the coated kaolin was placed in a line across the plate. The plate was then incubated for about 48 hours. A zone of biocidal activity was noted in proximity to the clay granules. Control plates using untreated kaolin clay did not show any inhibition of mold growth.

Example 7

Evaluation of Mold Prevention by Three Quaternary Ammonium Chloride Salt Formulas Three quaternary ammonium chloride salt formulas were tested to determine whether they could prevent mold growth on wall board core matrix containing dextrose and starch. The formulas were designated Q0240, Q426, and Q6141, respectively. Table 12 below shows each quaternary ammonium chloride salt and its composition.

TABLE 12

| Formula | Quaternary Ammonium Salt | Stock (PPM) | | Stock Sub-Fraction (PPM) |
|---|---|---|---|---|
| Q0240 | Alkyl dimethyl benzyl ammonium chloride | 320,000 | | |
| | Alkyl dimethyl benzyl ammonium chloride sub-fractions | | $C_{12}$ | 12800 |
| | | | $C_{14}$ | 297600 |
| | | | $C_{16}$ | 9600 |
| | Didecyl dimethyl ammonium chloride | 480,000 | | |
| Q426 | Alkyl dimethyl benzyl ammonium chloride | 320,000 | | |
| | Alkyl dimethyl benzyl ammonium chloride sub-fractions | | $C_{12}$ | 12800 |
| | | | $C_{14}$ | 297600 |
| | | | $C_{16}$ | 9600 |
| | Octyl decyl ammonium chloride | 240,000 | | |
| | Diacetyl dimethyl chloride | 120,000 | | |
| | Didecyl dimethyl chloride | 120,000 | | |
| Q6141 | Alkyl dimethyl benzyl ammonium chloride | 800,000 | | |
| | Alkyl dimethyl benzyl ammonium chloride sub-fractions | | $C_{12}$ | 40,000 |
| | | | $C_{14}$ | 480,000 |
| | | | $C_{16}$ | 240,000 |
| | | | $C_{18}$ | 40,000 |

Test samples having different quantities of the formulas were prepared by blending components listed in Table 13 below. For each test sample, starch, dextrose, and water, along with the defined concentration of one antimicrobial formula—either A0240, Q426, or Q6141 (except for the control test sample)—were blended separately then mixed together with the stucco. The antimicrobial formulas were added at a 10-fold dilution of stock (80 mg/g active). Following the addition of the stucco, the test sample mixture was vigorously stirred using a spatula to assure even distribution. Each mixture was then evenly disbursed into three plastic molds as quickly as possible to cast samples for testing.

TABLE 13

| Test Sample | Stucco (g) | Starch (g) | Dextrose (g) | Water (g) | Anti-microbial (g) | Total Weight (g) |
|---|---|---|---|---|---|---|
| Control | 100 | 0.375 | 0.125 | 87.5 | 0 | 188 |
| 250 ppm | 100 | 0.375 | 0.125 | 87.01 | 0.59 | 188 |

TABLE 13-continued

| Test Sample | Stucco (g) | Starch (g) | Dextrose (g) | Water (g) | Anti-microbial (g) | Total Weight (g) |
|---|---|---|---|---|---|---|
| 500 ppm | 100 | 0.375 | 0.125 | 87.32 | 1.18 | 188 |
| 1000 ppm | 100 | 0.375 | 0.125 | 85.14 | 2.36 | 188 |
| 2000 ppm | 100 | 0.375 | 0.125 | 82.8 | 4.72 | 188 |

After set-up, all test samples were placed in an 80° C. oven overnight to remove excess water. Upon drying, all samples were removed from molds by inversion and a sharp impact on a hard surface. After separation from molds, samples were placed in labeled weighing boats. FIG. 1 shows the concentration of quaternary ammonium chloride salts added to the wallboard core matrix.

Three or four test samples from each mixture presented in FIG. 1 were saturated with deionized water. Test samples were then inoculated with *Aspergillus fumigatus* spores. Inoculated samples were transferred to plastic tubs to which lids could be tightly fixed for incubation. Paper towels were placed in the bottom of each container and saturated with water prior to the addition of test samples.

Test samples prepared using formula Q0240 were inoculated Dec. 18, 2006 and incubated at room temperature. Test samples prepared using formulas Q426 and Q6141 were prepared and inoculated on Jan. 9, 2007 and Jan. 17, 2007, respectively. The latter two sets of test samples were incubated at 30° C., unlike the Q0240 samples, to facilitate and shorten the time of mold development. All test samples were photographed on Feb. 23, 2007. All test samples showed that water had moved up through the gypsum by capillary action, causing the surface of each sample to become moist, thereby creating conditions whereby mold could grow.

Formula Q0240 was found to be ineffective as a mold inhibitor. Mold growth was noted on the control sample, as well as the test samples including 250 ppm, 1000 ppm, and 2000 ppm of the formula.

Unlike formula Q0240, formulas Q426 and Q6141 exhibited mold inhibition, with Q6141 being concentration dependent. Formula Q426 prevented the growth of *Aspergillus fumigatus* at all concentrations tested—250 ppm, 500 ppm, 1000 ppm, and 2000 ppm. Some discoloration was noted, which could indicate limited mold growth. However, visible spore forming structures indicative of mold growth could not be detected with a 20× stereo microscope. Incorporation of Q6141 produced a concentration dependent anti-mold effect. Addition of Q6141 at a concentration of 250 ppm did not result in mold inhibition. Mold inhibition was detectable when Q6141 was added at 500 ppm and above (1000 ppm and 2000 ppm). Thus, the inhibitory properties of formula Q6141 appeared to be less than that of Q426.

Without wanting to be bound by theory, the antimicrobial effectiveness of Q426 and Q6141 are likely a reflection of the long hydrocarbon side chain of the $C_{16}$ and $C_{18}$ alkyl dimethyl benzyl ammonium chloride salts and the octyl decyl dimethyl ammonium chloride salt. Of the absolute amount of quaternary amine salts added to the core matrix, the octyl decyl ammonium chloride salt component of Q426 represented 30%, whereas the $C_{16}$ component of Q6141 represented only 5%. This difference appeared to be reflected in the mold challenge results, i.e., Q426 was more effective.

The results indicate the utility of adding either formula Q426 or Q6141 to wallboard core material for the prevention of mold growth. It is well understood that core matrix, having as part of the constituent material a carbohydrate source, will readily support mold growth given the right conditions.

Example 8

Method for Application of Quaternary Ammonium Salts

A stock solution containing quaternary ammonium salt was applied to paper face of assembled wallboard just before entering kiln for drying. The stock solution was applied using a spray bar apparatus similar to the box style header presented below. The amount of solution applied ranged from 0.25 to 4% of the weight of the dry paper per wallboard face. The concentration of active quaternary ammonium salt in the stock solution ranged from 4 to 20 mg/square foot of wallboard paper. Ideally the amount of quaternary ammonium salt per square foot ranged from 6 to 14 mg/square foot with 10 to 12 mg/square foot being the best concentration.

A system was used such that solution could be evenly applied laterally across the wallboard sheet at a line speed of 400-500 ft per min.

Example 9

Method for Blending Quaternary Ammonium Salts 3500 g of quaternary ammonium salt (for example, Formula Q6141 described in Example 7, above) was blended with 12.300 g of water. After blending about 3500 g of calcium aluminosilicate having a particle size >300 microns was added. The mixture was blended to form thick slurry, preferably a motorized metal mixing device. After blending, the slurry was poured out onto long strips of aluminum foil on the floor of a laboratory and allowed to dry for two weeks. Dry lumps of calcium aluminosilicate were then aggregated and placed in metal containers that were placed in an 80 degree centigrade incubator for about 1 week to dry further.

Lumps and powdered matrix were sent for further processing to another facility. All material was ground and jet milled. Particles after jet milling had an approximate size of 5 microns and less.

Quaternary ammonium salt coated aluminosilicate particles were subsequently blended with vinyl and other types of polymers and formed into rolled or extruded rigid high-impact films.

The objective was to form plastic materials upon which molds, algae and other microbes could not grow, i.e., the antimicrobial quaternary ammonium salt would become integral to the product and be present on the surface or slowly leech from the surface in an aqueous environment that could promote aforementioned organisms.

Example 10

Spray Nozzle Characterization for an Antimicrobial Coating Application

In one embodiment of the current invention, a quaternary ammonium salt as described herein may be applied evenly to a wallboard without effecting the appearance of the end product.

The nozzles used for this testing is an air actuated automatic spray nozzle (for example, the Spraying Systems Co. AA22AUH-SS air actuated automatic spray nozzle). The nozzle may include an air actuated shut off cylinder that is capable of cycling the nozzle at a rate of 180 cycles per minute. These nozzles will accept many types of spray tips. For this testing TPU style flat spray tips were used.

Prior to testing a test fixture was fabricated by Spraying Systems Co. This test fixture was mounted to an integrated conveyance system. The header was fabricated such that the nozzle spacing and gun to bed distance was easily adjustable. This allowed the examination of the effects of position of the nozzles on the wet coating characteristics. The sample material was fixed to the conveyor and traversed at a speed of 400 ft/min to simulate process conditions as closely as possible. The on/off operations of the nozzles were automatically triggered to spray the target area as it passed under the nozzle header. Liquid flow to the system was supplied using a pressure vessel. Liquid pressures were measured and monitored with 0-100 psig pressure transducers.

A self-contained, modular spraying system that enhances the performance of automatic spray guns may be used to control the operation of the spray gun as well as to control the liquid pressure (for example, the AutoJet® Modular Spray System). Consisting of two basic components, an electrical control panel and a pneumatic control panel, the modular system provides the power of a fully integrated system.

All preliminary testing was performed spraying water. Final testing was conducted using a quaternary ammonium salt as described herein.

Initial testing was conducted spraying water on sheets of white paper using spray tips (in this example, three TPU110003-SS spray tips). The solution was dyed, using food coloring, so that the spray pattern would be visible on the paper. During this testing it was determined that the spray distribution with the initial nozzle height and spacing was not providing an even distribution. After some trial and error the nozzle spacing was changed to 9.5 inches with a spray height of 9 inches. This seemed to provide an even distribution. At this point Trials were conducted spraying these nozzles at 80 psi (0.047 gpm per nozzle) on samples of wall board. The appearance of these samples was favorable.

Further testing was then conducted keeping the spray height and spacing constant but changing the spray tips to TPU-1100050-SS. This was done to increase the amount of fluid added to the wall board. This setup was sprayed at 60 psi (0.060 gpm per nozzle). Samples made under these conditions were also viewed as acceptable.

The purpose of these tests was to determine the operating conditions that would provide an even distribution of material across a 48 inch width of wallboard at speeds of 400 ft/min. The results of this testing showed that 6 nozzles spaced 9.5 inches apart at a spray height of 9 inches spraying 110 degree spray angle nozzles will achieve the required results. The capacity size of these nozzles will vary between 0033 and 0050 depending on the desired flow.

REFERENCES CITED

The entire content of each of the following documents is hereby incorporated by reference.

U.S. PATENT DOCUMENTS

| U.S. Patents | |
|---|---|
| U.S. Pat. No. 3,970,755 | Gazzard et al. |
| U.S. Pat. No. 4,661,503 | Martin et al. |
| U.S. Pat. No. 4,725,623 | Whitekettle et al. |
| U.S. Pat. No. 4,906,385 | Lyons et al. |

-continued

| U.S. Patents | |
|---|---|
| U.S. Pat. No. 5,041,463 | Whitekettle et al. |
| U.S. Pat. No. 5,457,083 | Muia et al. |
| U.S. Pat. No. 5,508,454 | Brancq & Boiteux |
| U.S. Pat. No. 5,561,187 | Bechara & Baranowski |
| U.S. Pat. No. 6,414,159 | Sano et al. |
| U.S. Pat. No. 6,664,224 | Kourai et al. |
| U.S. Pat. No. 6,680,127 | Capps |
| U.S. Pat. No. 6,767,647 | Swofford, et al. |
| U.S. Pat. No. 6,890,968 | Rabasco, et al. |
| U.S. Pat. No. 6,893,752 | Veeramasuneni, et al. |

U.S. Patent Applications

U.S. Patent Publication No. 20040033343

OTHER PUBLICATIONS

El-Zayat and Omran, "Disinfectants Effect on the growth and Metabolism of *Acetobacter aceti*," *Egypt J-Food-Sci.*, 11(1-2), 1983, pp. 123-128.

*Handbook of Biocide and Preservative Use*, Edited by H. W. Rossmore, Blackie Academic & Professional, 1995, pp. 361-362.

What is claimed is:

1. A method for preparing quaternary ammonium cations, wherein the quaternary ammonium cations have the formula:

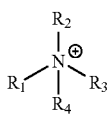

wherein:

$R_1$ is a straight-chain or branched-chain alkyl group having the formula $C_nH_{2n+1}$, wherein $17 \leq n \leq 30$, $R_2$ is an alkyl group selected from the group consisting of (a) straight-chain or branched-chain alkyl groups having the formula $C_nH_{2n+1}$, wherein $1 \leq n \leq 6$; (b) cycloalkyl groups or alkyl substituted cycloalkyl groups having the formula $C_nH_{2n-1}$, wherein $3 \leq n \leq 10$, and (c) benzyl or substituted benzyl groups, $R_3$ is an alkyl group selected from the group consisting of (a) straight-chain or branched-chain alkyl groups having the formula $C_nH_{2n+1}$, wherein $1 \leq n \leq 6$, (b) cycloalkyl or alkyl substituted cycloalkyl groups having the formula $C_nH_{2n-1}$, wherein $3 \leq n \leq 10$, and (c) benzyl or substituted benzyl groups, and $R_4$ is an ω-hydroxyalkyl group having the formula $[(CH_2)_mO]_nH$, wherein $2 \leq m \leq 6$ and $1 \leq n \leq 4$, comprising:

taking one mole equivalent of an alcohol, $R_4$—OH, wherein:
$R_4$ is defined as above;

cooling the alcohol to below 10° C. to give a cooled alcohol;

mixing the cooled alcohol with sufficient strong acid, also cooled below 10° C., to give about 1 mole equivalent of hydrogen ions;

adding to the alcohol-strong acid mixture a metal halide solution containing about 1 mole equivalent of halide ions in sufficient water to facilitate mixing, and stirring the resultant mixture until it is homogeneous or uniform:

adding about 1 mole equivalent to the mixture with stirring of a tertiary amine, $R_1$—$NR_2R_3$, wherein $R_1$, $R_2$ and $R_3$ are defined as above; and heating the resultant mixture to at least 60° C. to complete the reaction.

2. The method of claim 1, wherein the strong acid is sulfuric acid.

3. The method of claim 1, wherein the metal halide is sodium chloride.

4. The method of claim 1, wherein the temperature of cooling is 4° C.

5. The method of claim 1, wherein the temperature of heating is between about 70-100° C.

* * * * *